United States Patent
Brennan et al.

(10) Patent No.: US 8,777,614 B2
(45) Date of Patent: *Jul. 15, 2014

(54) CLOSED LOOP SPEED CONTROL FOR A PNEUMATIC DENTAL HANDPIECE

(71) Applicant: Dentsply International, Inc., York, PA (US)

(72) Inventors: Kevin Brennan, Villa Park, IL (US); Timothy M. Beck, York Haven, PA (US); Eugene J. Novak, Deerfield, IL (US); Thomas E. Barker, Cherry Valley, IL (US); William Raymond, Palatine, IL (US); Karl H. Bethke, Palatine, IL (US)

(73) Assignee: Dentsply International Inc., York, PA (US)

( * ) Notice: Subject to any disclaimer, the term of this patent is extended or adjusted under 35 U.S.C. 154(b) by 220 days.

This patent is subject to a terminal disclaimer.

(21) Appl. No.: 13/662,593

(22) Filed: Oct. 29, 2012

(65) Prior Publication Data

US 2013/0052606 A1 Feb. 28, 2013

Related U.S. Application Data

(63) Continuation of application No. 11/836,229, filed on Aug. 9, 2007, now Pat. No. 8,303,304, which is a continuation-in-part of application No. 11/612,128, filed on Dec. 18, 2006, now abandoned.

(60) Provisional application No. 60/772,103, filed on Feb. 10, 2006.

(51) Int. Cl.
*A61C 1/02* (2006.01)
*A61C 1/00* (2006.01)
*A61C 1/08* (2006.01)
*A61C 1/05* (2006.01)

(52) U.S. Cl.
CPC . *A61C 1/003* (2013.01); *A61C 1/05* (2013.01); *A61C 1/0015* (2013.01); *A61C 1/08* (2013.01); *A61C 1/0038* (2013.01)
USPC .......................................................... 433/98

(58) Field of Classification Search
USPC .............................. 433/100, 98, 101, 132, 99
See application file for complete search history.

(56) References Cited

U.S. PATENT DOCUMENTS

| | | |
|---|---|---|
| 3,676,931 A | 7/1972 | Pietschmann |
| 3,865,505 A | 2/1975 | Flatland |

(Continued)

FOREIGN PATENT DOCUMENTS

AT 389633 B 1/1990

OTHER PUBLICATIONS

PCT International Search Report; Jul. 9, 2009.

*Primary Examiner* — Sunil K Singh
(74) *Attorney, Agent, or Firm* — McNees Wallace & Nurick LLC

(57) ABSTRACT

A detection system for remotely determining the speed of a rotating tool tip in a pneumatic dental handpiece. A means for detecting the speed of the rotating tool tip monitors a periodic mechanical function at the pneumatic hose connected to the handpiece. The monitored periodic mechanical function serves to provide feedback that is used to control the speed of the rotating tool tip. The means for detecting the speed of the rotating tool detects a mechanical function of the rotating tool tip, which in transmitted to a controller. The controller in turn regulates the operation of an air supply valve in response to the detected mechanical function. The valve regulates the flow of air to the handpiece. By continuously adjusting the flow of air through the valve into the pneumatic hose, the speed of the rotating tool is maintained at the desired cutting speed.

20 Claims, 6 Drawing Sheets

(56) References Cited

U.S. PATENT DOCUMENTS

| | | | | |
|---|---|---|---|---|
| 4,052,649 A | | 10/1977 | Greenwell et al. | |
| 4,201,051 A | * | 5/1980 | Hall | 60/407 |
| 4,403,958 A | | 9/1983 | Lohn | |
| 4,403,959 A | | 9/1983 | Hatakeyama | |
| 4,417,875 A | | 11/1983 | Matsui | |
| 4,479,182 A | | 10/1984 | Beier | |
| 4,493,643 A | | 1/1985 | Tachibana | |
| 4,674,535 A | | 6/1987 | de Menibus | |
| 4,744,752 A | | 5/1988 | Nakayama et al. | |
| 4,764,114 A | * | 8/1988 | Jeffcoat et al. | 433/72 |
| 4,791,940 A | | 12/1988 | Hirschfeld et al. | |
| 4,893,067 A | | 1/1990 | Bhagwat et al. | |
| 4,949,745 A | | 8/1990 | McKeon | |
| 5,107,899 A | | 4/1992 | Murphy | |
| 5,201,899 A | | 4/1993 | Austin, Jr. et al. | |
| 5,295,825 A | | 3/1994 | Betush | |
| 5,332,194 A | | 7/1994 | Austin, Jr. et al. | |
| 5,364,227 A | | 11/1994 | Franetzki et al. | |
| 5,482,462 A | | 1/1996 | Rosenstatter | |
| 5,496,173 A | | 3/1996 | Wohlgemuth | |
| 5,538,423 A | | 7/1996 | Coss et al. | |
| 5,567,154 A | | 10/1996 | Wohlgemuth | |
| 5,934,904 A | * | 8/1999 | Elrod et al. | 433/88 |
| 5,980,248 A | | 11/1999 | Kusakabe et al. | |
| 6,390,815 B1 | | 5/2002 | Pond | |
| 6,722,881 B1 | | 4/2004 | Altendorf et al. | |
| 2004/0115591 A1 | * | 6/2004 | Warner | 433/98 |
| 2006/0063127 A1 | | 3/2006 | Gugel et al. | |
| 2008/0166685 A1 | | 7/2008 | Rosenblood et al. | |

\* cited by examiner

CLOSED LOOP SPEED CONTROL FOR A PNEUMATIC DENTAL HANDPIECE

FIELD OF THE INVENTION

The present invention is directed to apparatus for controlling the rotational speed of a pneumatic dental handpiece by detecting and monitoring a periodic mechanical function produced by the handpiece.

BACKGROUND OF THE INVENTION

In dental treatments with current pneumatic handpieces, a tool tip or burr is rotated at a speed higher than the desired cutting speed. These speeds can be as high as 450,000 revolutions per minute (rpm). When cutting load is applied, this pneumatic system is slowed significantly, adversely affecting cutting capability. The dental practitioner must maintain a useful system speed for cutting by carefully balancing cutting load and pneumatic pressure in order to properly accomplish the cutting operation. Water is also typically provided during the cutting operation to cool the cutting surface as well as the tool surface.

Knowledge of the speed of the rotating burr and/or the rotating turbine under load is desirable and necessary to control speed at a useful value. Prior art devices detect the rotating speed of a pneumatic handpiece by a magnetic resistance element, or elastic control elements assembled near the tool tip.

For example, U.S. Pat. No. 5,567,154 issued to Wohlgemuth on Oct. 22, 1996, entitled "Dental Turbine Drive Having Means of Automatic Speed Control," (the '154 patent) and U.S. Pat. No. 5,496,173 issued to Wohlgemuth on Mar. 5, 1996, entitled "Dental Handpiece Having an Automatically Controlled Turbine Drive," (the '173 patent) both disclose speed control by a control element in the form of a proportional valve placed in an air turbine exhaust path that throttles open as the turbine speed is decreased due to lowered centrifugal force on an elastic element, and conversely throttles closed as the turbine speed is increased. The control element adds cost and complexity to the handpiece. Such a control element also is subject to degradation during sterilization of the handpiece. The '154 patent further includes as a second element a pressure chamber that responds to changes in pressure to further support the control element. Devices incorporating these features are currently being marketed.

U.S. Pat. No. 4,493,643 issued Jan. 15, 1985, to Tachibana, entitled "Dental Handpiece Having Non-contact Rotational Speed Detection Device" (the '643 patent) discloses speed detection by a cylindrical rotor of magnetic material and coil windings to produce an induction pulse generator. Such detection means adds cost and complexity to the handpiece and also is subject to degradation during required sterilization of the handpiece.

U.S. Pat. No. 3,865,505 issued to Flatland on Feb. 11, 1975, entitled "Speed Governor for a Dental Handpiece," (the '505 patent) discloses speed control by a proportional bypass valve placed in the turbine supply path that throttles open as the turbine speed is decreased due to lowered discharge pressure in the exhaust channel, and conversely throttles closed as the turbine speed is increased. It too is inferior because it adds cost and complexity to the handpiece, and its control apparatus is subject to degradation during sterilization of the handpiece. Devices incorporating these features are currently being marketed.

These prior art methods are impractical or undesirable as they add cost to the handpiece. These devices also can require relatively large structures within the handpiece, making them difficult and uncomfortable to hold, while also leading to integration problems as a result of this bulky but required size. Depending on the design, the sensors/control elements of these prior art units also can be difficult to protect from damage during handpiece sterilization. What is desired is a detection system that remotely detects the drill speed and regulates the drill speed based on the detected drill speed. Such a system does not rely on detecting exhaust pressure to determine rotational speed. Ideally, the detection system is not subject to damage as a result of handpiece sterilization.

SUMMARY OF THE INVENTION

A detection system remotely determines the speed of a rotating tool tip in a pneumatic dental handpiece. The present invention does not rely on a control element operated by exhaust air pressure that is installed in a handpiece. The dental handpiece has a proximal end and a distal end, the rotating tool tip, also referred to as a bur, being located at the distal end. A means for detecting the speed of the rotating tool tip monitors a periodic mechanical function at a location away from the distal end of the handpiece, such as at or within a fluid hose, such as a pneumatic hose, connected to the handpiece. The monitored periodic mechanical function is related to the rotational speed of the tool tip. The monitored periodic mechanical function serves to provide feedback that is used to control the speed of the rotating tool tip.

The means for detecting the speed of the rotating tool is in communication with a controller. It detects a mechanical function associated with the rotating tool tip, which is transmitted to the controller, typically as a signal. The controller receives the signal, calculates the rotational speed of the rotating tip, compares the calculated speed to a pre-set speed range and regulates the operation of a fluid supply valve in response to the detected mechanical function by adjusting the valve to meter the flow of a drive fluid to maintain the rotational speed of the tip within the pre-set speed range. The valve thus regulates the flow of the drive fluid, preferably air under pressure, to the handpiece. By continuously adjusting the flow of the pressurized drive fluid through the valve, as required, into the pneumatic hose, the speed of the rotating tool is maintained within the desired cutting speed range.

The present invention relies on a means for detecting a mechanical function related to the speed of the tip, such as a vibration, that is located in the handpiece, or within the pneumatic hose attached to the handpiece, or in a coupling positioned between the pneumatic hose and the handpiece. Thus, it does not necessarily rely on "cylindrical rotor of magnetic material" and/or coil windings to produce an "induction pulse generator," which is difficult to sterilize. Neither does it depend upon a sensor being located within the handpiece that is susceptible to damage by sterilization. Since it is not installed in the handpiece, such as an elastic control element operated by centrifugal force, it does not require sterilization. The means for detecting speed being located remotely from the handpiece allows the handpiece size to be both smaller as well as ergonomically designed for the comfort of the user, here the dentist. Thus, the pneumatic handpiece of the present invention can duplicate the operating "feel" of more compact electric motor handpieces. Nevertheless, the present invention contemplates sensors that have high temperature capability that can survive repeated sterilizations so that they can be installed within the handpiece.

Another advantage of the present monitoring and feedback system of the present invention is that increased torque and power will be delivered by the pneumatic handpiece delivered over a wider range of operating speeds during its use.

Still another advantage of the present invention is that the tool tips, typically burs and diamonds, will have a longer life. Since the pneumatic motor can operate at a lower speed, the handpiece itself also should have a longer life in addition to generating less noise during free-running operation.

Other features and advantages of the present invention will be apparent from the following more detailed description of the preferred embodiment, taken in conjunction with the accompanying drawings which illustrate, by way of example, the principles of the invention.

DETAILED DESCRIPTION OF THE INVENTION

Figure 1:
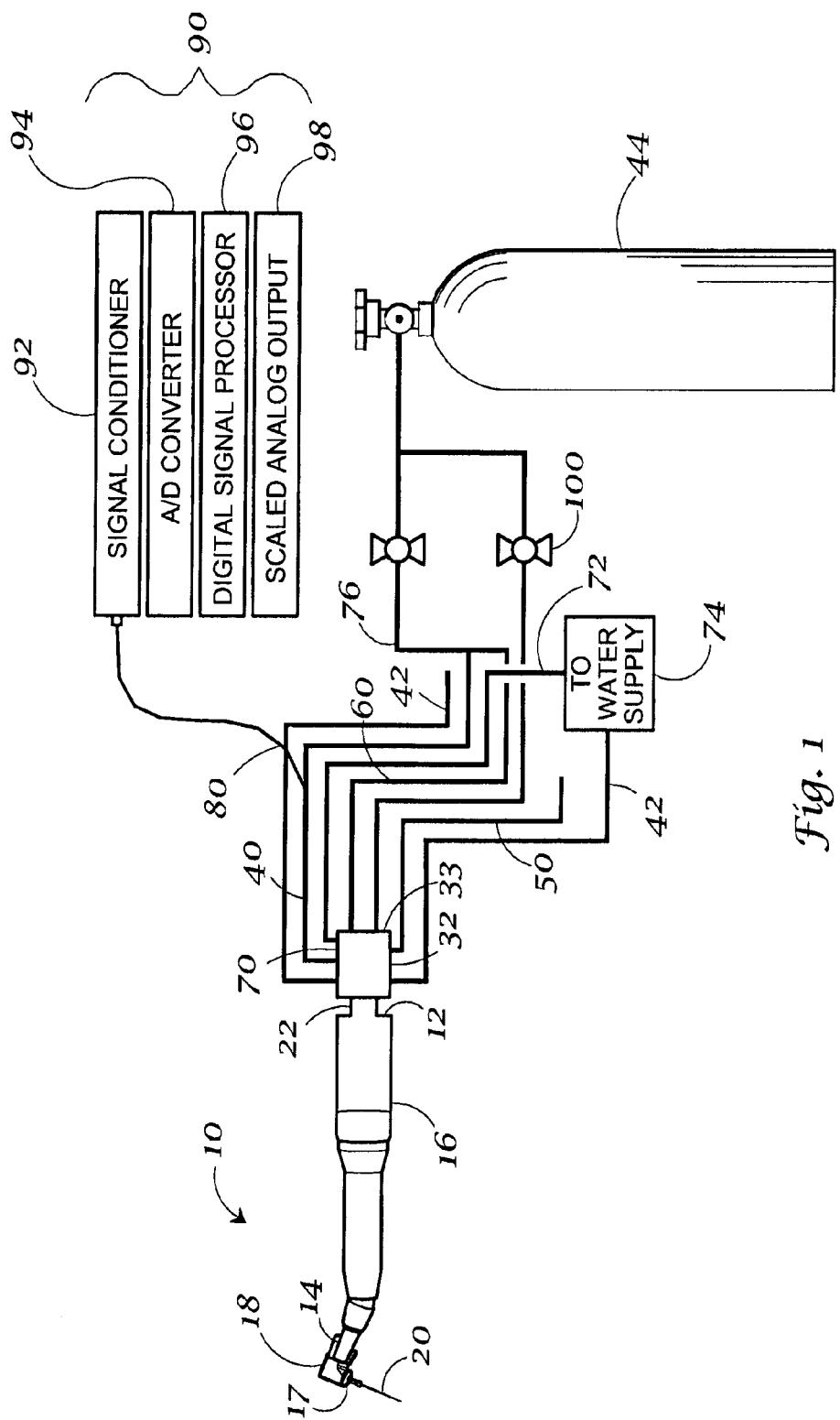
FIG. 1 is a schematic cross sectional view of the control system for a dental handpiece of the present invention.

The present invention comprises a pneumatic dental handpiece 10 coupled to a pneumatic supply hose 40. The dental handpiece 10 has a proximal end 12, a distal end 14 and a body 16 extending between the proximal end 12 and the distal end 14. A handpiece head 18 is located at the distal end 14, the head housing a rotating turbine assembly 17 into which is inserted a bur 20 or tool tip. Bur 20, on assembly into head 18, extends away from the distal end 14 of the handpiece 10. Depending on the handpiece design, the bur can extend substantially parallel to an axis through handpiece 10, the axis extending between the proximal end 12 and the body 16 of the handpiece. The bur may extend substantially perpendicular to this axis. Alternatively, the bur may extend at any angle therebetween. As shown in FIG. 1, the bur extends at an angle to the axis between parallel and perpendicular. The proximal end 12 of the handpiece 10 includes a handpiece coupling 22 designed to interface with a pneumatic hose coupling 32 forming a first end of pneumatic hose 40, thereby forming an airtight joint that supplies air to the rotating turbine assembly through a drive air passageway in the handpiece extending from the proximal end to the distal end. The pneumatic supply hose 40 preferably is flexible, having a first coupling end 33 and an opposed second end 42 connected to a pressurized air supply 44 by any suitable coupling.

The pneumatic supply hose 40 includes an air supply passageway 60 and an exhaust passageway 50 for providing drive air to the handpiece. An air supply control valve 100 is connected to the air supply passageway 60, as shown for example in FIG. 1 at the second end 42 of the supply hose 40, to regulate the flow of drive air from air supply 44 into air supply passageway 60. A water supply passageway 72 connected to a water supply 74 may also be included in supply hose 40, or a separate water supply hose connected to a water supply may be provided. Drive air from air supply 44 passes through supply valve 100 into air supply tube 60 and into the handpiece 10 to drive the turbine and attached bur. The drive air is directed from the proximal end 12 of the hand piece 10, through the handpiece to the distal end 14 where it is used to drive turbine assembly 17 and thereby tool tip 20. Return air is then transported through the handpiece to the proximal end and then to the exhaust tube 50, where it is exhausted remotely from the handpiece. A separate supply of pressurized air sometimes referred to as chip air, may be provided to interact with the water supply to provide a water spray through a separate chip air supply passageway 76. A fine mist water spray can be achieved at the distal end by placing the water supply passageway 72 coaxially and within the chip air supply passageway 76.

It will be understood by those skilled in the art that while pneumatic hose 40 is shown with an air supply passageway 60 and an exhaust passage way 50, any equivalent structure that transports drive air from air supply 44 through a valve to the handpiece 10 to drive bur 20 and then exhausts the air from the handpiece may be utilized. One such structure may include a separate air supply tube and a separate exhaust tube or port.

The present invention further includes a means for detecting a mechanical function 7. As used herein, a mechanical function is any periodic mechanical artifact that is generated by operation of the handpiece 10. A mechanical artifact includes but is not limited to any periodic mechanical vibration of the handpiece, a pressure, an acoustic wave or an oscillation resulting from its operation. The means for detecting may also include an electrical or a magnetic speed detection means, or combination of electrical and mechanical speed detection means in the handpiece that provides an indication of rotational speed of the bur or turbine in a periodic fashion, and is used as a basis to adjust the rotational speed of the bur to attempt to maintain the speed of the bur as a load is applied to the bur. In a preferred embodiment, the mechanical function detected is the periodic vibration of the rotating tool transmitted through the handpiece, and preferred means for detecting this mechanical function is an accelerometer. However, depending upon the mechanical function monitored, the means for detecting may vary. The means for detecting can include any sensor that can detect and monitor a periodic mechanical function, such as a pressure transducer, a sound transducer, a linear variable differential transformer (LVDT), a microphone or an acoustic device for detecting acoustic transmissions from operation of the handpiece. A pressure transducer may be used to detect the mean pressure in the handpiece. Alternatively, the pressure transducer may be used to detect the difference in pressure between the inlet and outlet pressure or to detect pressure pulsations. The means for detecting may also be any means (optical or other) for detecting periodic vibrations in the handpiece, since such vibrations are indicative of the tool tip rotational speed. The means for detecting may also be an optical speed detection means to detect an optical signal from an optical signal generator associated with the rotating tool. The means for detection may also be a Hall Effect detector that uses magnetic and electrical impulses to determine rotational speed. In a Hall Effect device, a rotating magnet generates an electrical field, which field can then be detected.

The means for detecting a mechanical function 70 is a detector that preferably is located in the pneumatic hose coupling 32. However, its location is not so restricted and it may alternatively be located in the flexible supply hose 40 or in the pneumatic handpiece 10 itself, although a proximal end location 12 may be preferable when size is a consideration.

Figure 2:
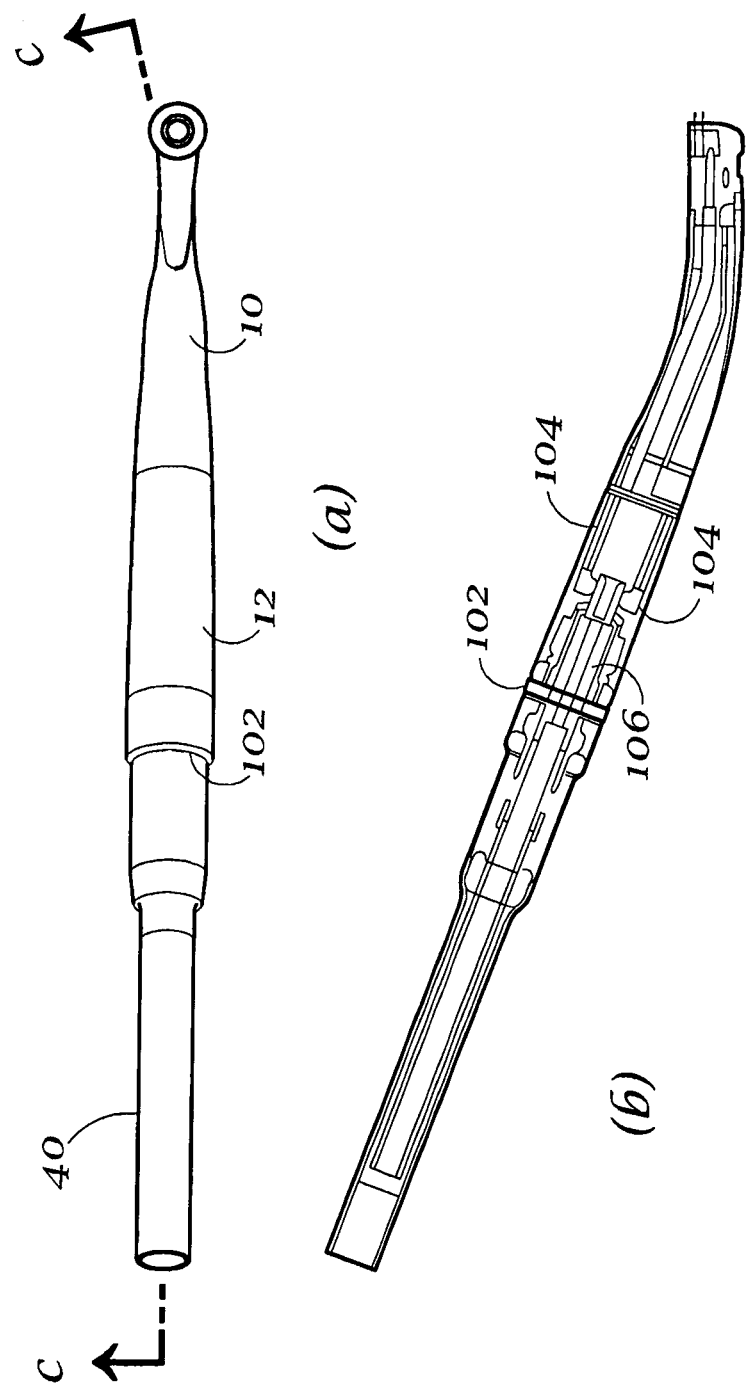
FIG. 2 is a schematic cross sectional view of a handpiece coupled to a supply hose using the novel coupling of the present invention.

In one preferred embodiment, the detector is located in a novel pneumatic hose coupling 102 depicted in FIG. 2a wherein the female assembly 104 is assembled to the proximal end 12 of handpiece 10, while the male assembly 106 is assembled to the supply hose 40. FIG. 2b is a cross-section of FIG. 2a along c-c. This novel coupling 102 includes a female assembly 104 and a male assembly 106. In FIG. 2, the female assembly 104 is assembled to the proximal end 12 of handpiece 10, while the male assembly 106 is assembled to the supply hose 40. This novel coupling 102 satisfies the prerequisites of a coupling, which include being a light weight and compact mechanism that permits quickly and properly connected the handpiece 10 to the supply hose 40, as well as allowing the handpiece to swivel on its connection during operation to prevent the hose from twisting. In addition, coupling 102 provides an additional mechanism to ensure that the proper handpiece is coupled to the supply hose and that the turbine supply air flow is properly restricted. Stated alternatively, coupling 102 prevents the air pressure provided to handpiece 10 from exceeding a predetermined limit. Coupling 102 also can be fabricated at a significantly lower cost. In addition, because of the novel design, the male assembly can be fabricated with a significant weight reduction. This further reduces fatigue experienced by the dental professional over the course of a workday.

Figure 3:
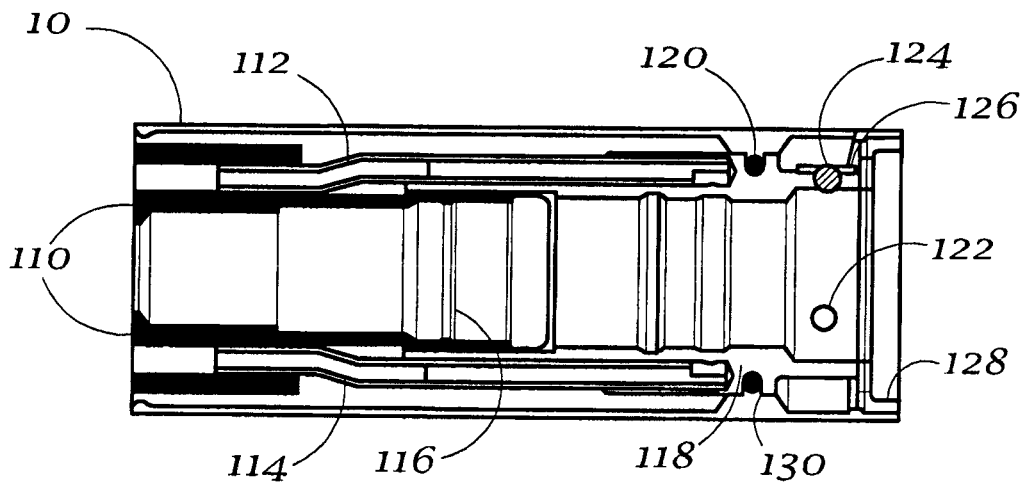
FIG. 3 is a cross-sectional view of the female assembly of the coupling of the present invention.
Figure 4:
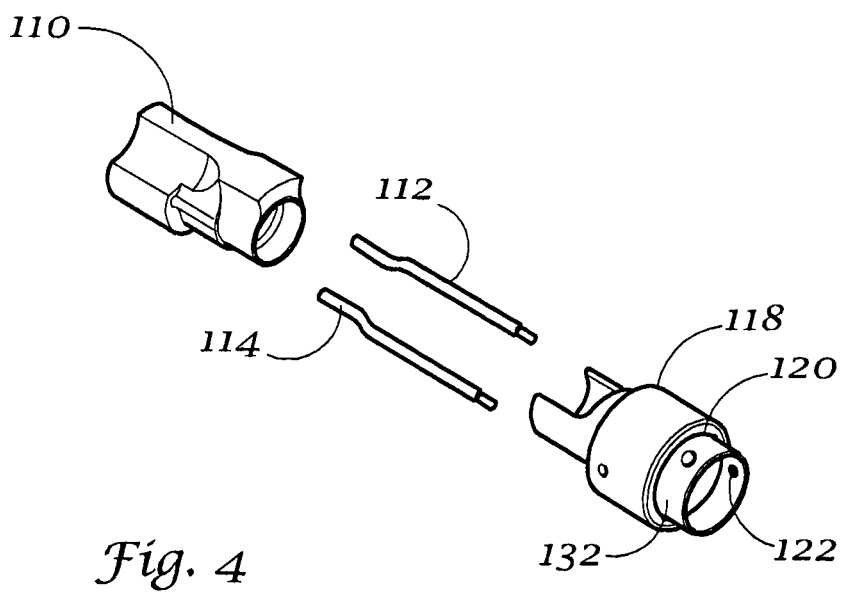
FIG. 4 is an exploded view of the female assembly of FIG. 3.
Figure 5:
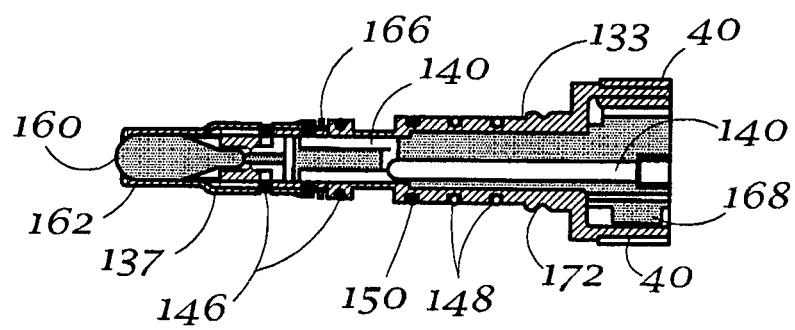
FIG. 5 is a cross-sectional view of the male assembly of the coupling of the present invention.
Figure 6:
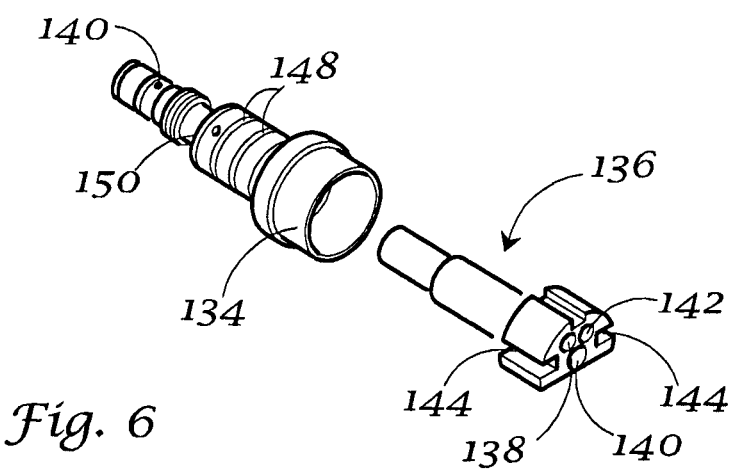
FIG. 6 is an exploded view of the male insert of FIG. 5.

FIGS. 3 and 4 depict female assembly 104 of coupling 102, while FIGS. 5 and 6 depict male assembly 106 of coupling 102. The coupling system is particularly suited for use with a dental handpiece having a detection system that remotely monitors the rotational speed of a tip, but is not so limited. Fundamentally, coupling 102 comprises female assembly 104 having a passageway for drive air to drive the handpiece tip comprising a diameter having a predetermined axial location, and a male assembly 106 that mates to the female assembly 104 and also having a passageway for drive air to drive the handpiece tip. The male assembly 106 further comprises a movable ring 164 having a first position that blocks the drive air passageway or port 140 of the male assembly 106 when the male assembly 106 is removed from the female assembly 104. The male assembly has a second position that retracts from the drive air passageway or port 140 when the male assembly 106 is assembled to the female assembly 104, thereby providing an aperture of predetermined size for flow of drive air from the drive air passageway in the male assembly 106 to the drive air passageway in the female assembly 104 as a result of movement of the ring 164 due to application of an external force that moves the ring, here contact with diameter 116 in the female assembly 104. A spring 166 biases ring 164 into the first position in which drive passageway or port 140 is closed when the external force is removed so that substantially no drive air moves through port 140. The applied external force is sufficient to counteract the spring force and allow the ring to move to the second position in which an aperture is opened. The applied external force is selected to counteract the spring force to provide an aperture having a preselected size. This is an important aspect of the invention, since this predetermined size permits flow of a predetermined amount of air. This predetermined amount of air determines the maximum air flow, and hence air pressure that is allowed to pass to the female assembly and hence to the handpiece from the male assembly.

FIG. 3 depicts a preferred embodiment of female assembly 104 assembled to the proximal end 12 of handpiece 10, while FIG. 4 is an exploded view of female assembly 104. A pair of tubes 112, 114, preferably stainless steel, is positioned between a front female coupler 110 and a rear female coupler 118. As depicted in FIGS. 3 and 4, conduit 112 is a chip air tube and conduit 114 is a chip water tube. However, depending upon the design of the handpiece, these may be interchanged. The chip water tube 114 and the chip air tube 112 are in fluid communication with the water supply passageway and the chip air supply passageway in the handpiece. Front female coupler 110 further includes a critical diameter 116 that controls the drive air pressure delivered to the handpiece, as will become evident. Female assembly 104 includes O-ring 120 assembled in groove 130 in rear female coupler 118. This groove 130 provides a seal between the inner diameter of the handpiece and the outer diameter of female assembly 104 at rear female coupler 118. Rear female coupler 118 further includes a plurality of apertures 122. FIGS. 3 and 4 depict three apertures 122 at about 120° along diameter 132 of rear female coupler, although more apertures or as few as two apertures can be located on this diameter. Each aperture houses a bearing 124 that permit free rotation of male assembly 106 inside of female assembly 104. These bearings are also captured in circumferential groove 172 of male insert 133, see FIGS. 5 and 8, permitting female assembly 104 to be quickly connected or disconnected from male assembly 106 by application of an axial force in the appropriate direction. Leaf spring 126 retains bearing 124 in position within aperture 122. Threaded nut 128 locks female assembly 104 within proximal end 12 of handpiece. Threaded nut may be used in conjunction with a thread adhesive applied to female assembly to provide additional safeguards to prevent the loosening of female assembly 104 within the handpiece over extended periods of time.

FIG. 5 depicts a cross-sectional view of male assembly 106 of the coupling of the present invention. Male assembly 106 comprises male insert 133, which further comprises male coupler housing 134 having an axial cavity and insert 136, and recognition valve assembly 137. FIG. 6 depicts an exploded view of male insert 133. Insert 136, preferably made of a plastic material, but which may be made from any suitable material, is introduced into the cavity of male coupler housing 134 which engages insert 136, preferably made from stainless steel, but which also may be made from any suitable material. Insert 136 is firmly affixed into male coupler housing 134 by any suitable means, which in the preferred embodiment is accomplished by adhesive bonding. Insert 136 includes a first end that is inserted into coupler housing 134 and a second end that includes a plurality of ports that supply air and water from supply hose 40. These ports include chip water port 138, drive air port 140, and chip air port 142. The male coupler housing 134 includes a pair of drive air seals 146, a pair of chip air seals 148 and a chip water seal. These seals direct the flow of these fluids into the appropriate regions of female assembly 104 when the male assembly 106 is properly assembled into female assembly 104. Male insert further includes exhaust air ports 44 to channel exhaust air from the handpiece. Electrical wiring conveniently may be channeled through these exhaust air ports 144 to other regions of the male assembly 106 or to the female assembly or to the handpiece itself. Male insert 133 further includes a sensor housing 168 to house the means for detecting a mechanical function 70, which preferably is a sensor. Counterbore 170 accepts a brass barb from the pneumatic supply hose 40, thereby capturing the hose to insert 136. When insert 136 is plastic, as in the preferred embodiment, a brass hose barb deforms into the plastic forming counterbore 170 and securing the barb to the counterbore. Thus, coupling 102 conveniently provides a design that not only permits rapid assembly and disassembly of the handpiece to the pneumatic hose supply, but also provides a desirable location to house the sensor so that it can perform its monitoring/feedback function, yet can be readily removed so that it is not subject to the harsh conditions of sterilization. Other advantages of the coupling are will become evident.

Figure 7:
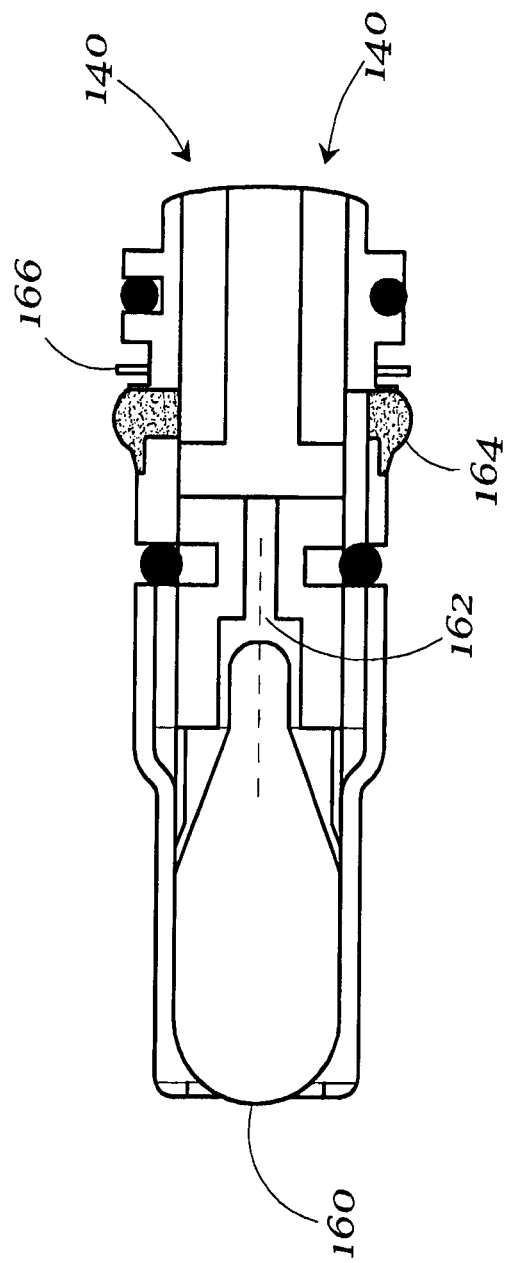
FIG. 7 is a cross-sectional view of the recognition valve assembly of the male assembly of FIG. 5.

FIG. 7 is a detailed cross-sectional representation of recognition valve assembly 137. In its simplest form, recognition valve assembly 137 is a body having a passageway for air that can communicate directly or indirectly with an air supply. The recognition valve assembly 137 further includes a ring 164 movable from a first position that blocks the air passageway to a second position that retracts from the drive air passageway, the second position providing an opening or aperture of predetermined size for flow of drive air from the drive air passageway of the male assembly and either directly or indirectly to the handpiece as a result of movement of the ring from a force external to the male assembly, the predetermined size of the opening providing a predetermined air flow and hence a maximum predetermined air pressure when the ring is in the second position. This maximum predetermined air pressure can be used to provide the handpiece with a pressure rating.

In a preferred embodiment, assembly 137 includes a light source 160, which is the source of light at the distal end of handpiece 10. Light is transmitted to the distal end by a fiber optic (not shown) in handpiece 10. Contact 162 provides an electrical connection for light source 160. Contact 162 can be connected to a power source by wires passing through the exhaust air ports 144 as previously discussed. Recognition valve assembly 137 further includes a drive air passageway or port 140 that extend to ring 164. This ring 164 is movable from a front position to a second position. When male assembly 106 is assembled into female assembly 104, seals 148 and 150 direct chip air and chip water from the supply hose through the male assembly 106 and into the appropriate tubes 112, 114 in the female assembly 104 and then into the handpiece. Seals 146 secure the passageways so that drive air passes from supply hose 40 into drive air port 140 in male insert 132 which continues into recognition valve assembly 137, female assembly 104 and into handpiece.

Recognition valve assembly 137 and its interaction with female assembly 104 provide the further advantage of controlling the flow of air, and hence the maximum air pressure flowing into handpiece 10. Ring 164 assembled onto recognition valve assembly 137 is movable. Spring 166 biases ring into a closed position when male assembly 106 is removed from female assembly 104. However, when male assembly 106 is inserted into female assembly 104 by application of the appropriate axial force, ring 164 in a preferred embodiment interacts with diameter 116 in female assembly 104 as bearings 124 are forced into groove 172 of male assembly, the action moving ring 164 and overcoming the biasing force of spring 166, thereby providing an opening for drive air flow from drive air passageway or port in male assembly 106 to drive air passageway in female assembly 104 and hence to handpiece 10. In as much as this opening is fixed, but predetermined, the amount of air flowing through the opening is also predetermined. Since the air flow is fixed by the interaction of ring 164 of male assembly 106 with diameter 116 of female coupling, the drive air flow is fixed, but can be modified. Thus, the coupling can provide a maximum air flow rate by controlling the interaction of ring 164 with diameter 116. To modify the flow of air, the relationship of diameter 116 and ring 164 is modified. In a preferred embodiment, diameter 116 is machined axially either closer to the handpiece or further from the handpiece to decrease or increase the size of the opening and hence the flow of air. Alternatively, the location of ring 164, the size of ring 164 or the geometry of ring 164 can be modified so that interaction with diameter will increase or decrease the size of the opening. In this way, the coupling can provide a maximum pressure rating for a handpiece. Thus, a handpiece can be provided with a coupling that rates the handpiece based on the maximum flow of drive air through the coupling at, for example, 45 psia, 50 psia, 55 psia and so on. While the preferred embodiment envisions application of force to ring 164 by diameter 116 to move ring 164 to second position, any other method or structure that applies force to ring 164 to bias the ring to second position is contemplated.

Figure 8:
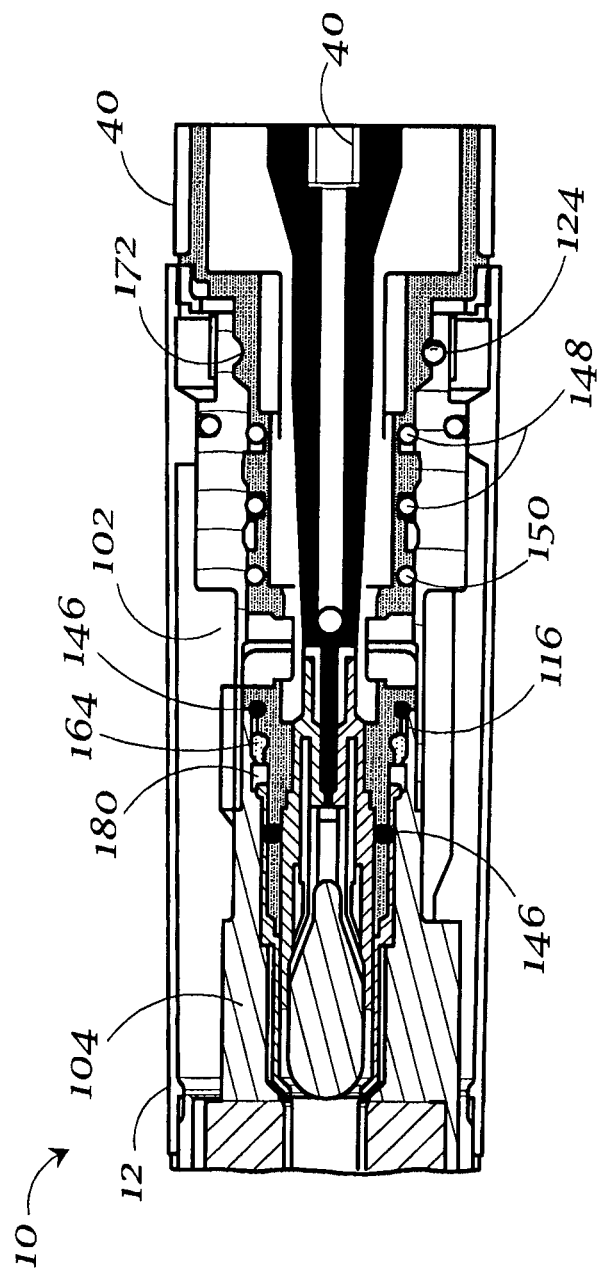
FIG. 8 depicts the coupling with the male assembly inserted into female assembly.

FIG. 8 depicts coupling 102 assembled, with male assembly 106 assembled into female assembly 104. Coupling 102 is assembled into proximal end 12 of handpiece 10, and supply hose 40 is attached to male assembly 106. Bearings 124 are seated into groove 172, providing the quick disconnect feature. As can be seen, seals 146, 148 and 150 provide pathways for drive air, chip air and chip water from supply hose 40 to handpiece 10. Ring 164 contacts diameter 116, moving ring 164 to create a opening 180 of predetermined size that determines the maximum predetermined air pressure of the handpiece through which drive air flows, as discussed above. A sensor or means for detecting a mechanical function 70 is housed in housing 168, not visible in FIG. 8, but visible in FIG. 5, located in coupling 102.

The present invention also contemplates detectors located in the distal end 14 when the detector or sensor can be sealed so that sterilization can be accomplished without damaging the detector or if the detector or sensor is otherwise capable of withstanding the harsh environment of repeated sterilizations. The detector can be unsealed if it is resistant to degradation due exposure to the fluids and temperatures used in the required sterilization procedures. The detector 70 is in communication with a controller 90. The signal detected by detector 70 is a periodic signal indicative of the rotational speed of tool tip 20 or air turbine assembly 17 that is transmitted to the controller 90. Although detector 70 is depicted as wired to controller 90 by means of embedded sensor wire leads 80, as shown in the accompanying FIG. 1, the present invention contemplates wireless communication between the detector 70 and the controller 90, such as by transmission of RF signals as is well known.

Controller 90 may include a signal conditioner 92, which conditions and amplifies the signal received from detector 70, an optional analog to digital (ND) converter 94, that converts an analog signal to a digital signal if the signal transmitted by the detector 70 is not digital, a digital signal processor 96, and a scaled analog output 98. Controller 90 is in communication with air supply valve 100, which is preferably an electronically controlled air supply valve. Such a valve can be controlled with a solenoid, for example. The output of the controller opens and closes the valve as required to maintain the speed of the tip within a predetermined range. Increasing or decreasing the amount of air from the air supply through air supply valve 100 increases or decreases the speed of the tip, which airflow is controlled by the feedback from detector 70. Since the speed of the bur is monitored by the sensor or detector 70, which is then used to vary the drive air from the air supply via controller 90 to maintain the bur or air turbine at a substantially constant speed, the result is a closed loop speed control system.

In a preferred embodiment, the closed loop control of a pneumatic dental handpiece is accomplished by sensing a periodic mechanical function of the handpiece indicative of the rotational speed of the tool tip, vibrations, generated by operation of the rotating tool tip 20 via a detector 70, such as an accelerometer, mounted in the hose coupling 32. The signal generated is delivered to the signal conditioner by wire leads 80 fed within the supply hose 40 back to the location of the supply valve 100. The conditioned signal then is filtered or narrowed to oscillations within the expected operating range of the instrument, and converted into a digital approximation. Within the controller 90, and specifically by digital signal processor 96, a Fourier Transform of the digital signal is calculated, and the fundamental frequency corresponding to rotational speed is selected via a logic algorithm. This rotational speed is compared against a pre-set operating speed target to calculate a proportional adjustment of the supply valve 100 to meter the proper volume of air through it.

The handpiece of the present invention that includes the closed loop control, when fitted with a coupling 102 provides the advantages of having a sensor that is readily removable so that the sensor is not subject to failure due to exposure to the harsh conditions of sterilization. Furthermore, if the sensor should fail, it is housed in male insert 133, so that the male insert can be removed from the hose assembly and replaced with a new male insert. Alternatively, the sensor 170 can be removed from the sensor housing 168 and replaced. Coupling permits the handpiece to be rated based on a maximum pressure, which somewhat simplifies the operation of the fluid supply valve in response to the detected mechanical function. By incorporating the maximum pressure rating of the handpiece, the algorithm can also limit the maximum pressure required from the fluid supply valve, simplifying the feedback to the fluid supply valve. Even if the algorithm does not provide this control, the mechanical features of the coupling will automatically control the air flow. In addition, the preferred coupling provides a quick disconnect feature, allowing the separation of the handpiece 10 from the pneumatic hose supply 40. Furthermore, the separation can be accomplished by the unique design of the male assembly and female assembly without having to close the supply of air from the supply hose.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A system for remotely monitoring the rotational speed of a rotating tip of a pneumatic dental handpiece, comprising:
   a dental handpiece having a proximal end and a distal end;
   a rotating tip located at the distal end of the handpiece;
   a light at the distal end of the handpiece;
   a fluid supply;
   a fluid conduit connected to the proximal end of the handpiece to provide fluid communication from the fluid supply to the handpiece to drive the rotating tip;
   a hose coupling attached at one end to the fluid conduit, and at the other end to the handpiece, the hose coupling further comprising
      a female assembly having a first passageway providing fluid communication with the tip, the first passageway having a diameter with a predetermined axial location,
      a male assembly having a second passageway providing fluid communication between the fluid conduit and the first passageway of the female assembly, wherein the fluid from the fluid supply is air for driving the tip, the male assembly further comprising a movable ring having a first position that blocks the second drive air passageway and communication to the female assembly when the male assembly is removed from the female assembly, and having a second position that retracts from the second drive air passageway when the male assembly is assembled to the female assembly, thereby providing an aperture of predetermined size for flow of drive air from the second drive air passageway in the male assembly to the first drive air passageway in the female assembly when the male assembly is assembled to the female assembly, a light source communicating light from the male assembly to the distal end of the handpiece by a fiber optic, and an additional passageway for exhaust air;
   a sensor for detecting the rotating tip speed of the tip;
   a control valve in the fluid conduit to regulate the flow of fluid from the fluid supply into the handpiece; and
   a controller in communication with the sensor and with the valve, wherein the controller receives a signal from the sensor, the controller comparing the detected speed to a preset speed range, and adjusts the control valve to meter fluid to the handpiece as required so that the rotating speed of the tip is maintained within the reset speed range.

2. The system of claim 1 further including sensor lead wires between the sensor and the controller to provide communication between the sensor and the controller.

3. The system of claim 1 further including an RF transmitter connected to the means for detecting and an RF receiver connected to the controller to provide communication between the means for detecting and the controller.

4. The system of claim 1 wherein the controller includes a signal conditioner to condition the signal received from the means for detecting.

5. The system of claim 4 wherein the controller includes a scaled analog output.

6. The system of claim 1 wherein the controller includes an analog to digital converter when the signal transmitted from the means for detecting is an analog signal.

7. The system of claim 1 wherein the controller includes a digital signal processor.

8. The system of claim 1 wherein the sensor is a Hall Effect device.

9. The system of claim 1 further including a water supply passageway in communication with a water supply.

10. The system of claim 1 further including a chip air supply passageway in communication with an air supply.

11. The system of claim 10 wherein a water-air mist is produced by cooperation of the water supply passageway and the chip air supply passageway.

12. The system of claim 1 wherein the sensor is located remotely from the distal end of the handpiece.

13. The system of claim 1 wherein the sensor is located in the proximal end of the handpiece.

14. The system of claim 1 wherein the sensor is positioned in the fluid conduit.

15. The system of claim 1 wherein the sensor is positioned in the hose coupling.

16. The system of claim 1 wherein the hose coupling further includes a spring biasing the movable ring to the first position blocking airflow to the first passageway when the male assembly is disassembled from the female assembly.

17. The system of claim 1 wherein the hose coupling further includes include a quick connect/disconnect apparatus for connecting the female assembly and the male assembly.

18. The system of claim 1 wherein the hose coupling further includes an additional passageway for chip air and a passageway for chip water.

19. The system of claim 1 wherein the hose coupling further includes a passageway for electrical wiring.

20. The system of claim 1 wherein the hose coupling further includes a sensor housing.

\* \* \* \* \*